United States Patent [19]
Schott et al.

[11] Patent Number: 6,079,678
[45] Date of Patent: Jun. 27, 2000

[54] INTRAVENOUS STAND SUPPORT ASSEMBLY

[76] Inventors: Jeffery C. Schott, 33 Sipple Ave., Baltimore, Md. 21238; Marc D. Schott, 9928 Richlyn Dr., Perry Hall, Md. 21128; Jeffrey D. Fox, 8290 Dwyer Rd., Howell, Mich. 48843

[21] Appl. No.: 09/176,323

[22] Filed: Oct. 22, 1998

[51] Int. Cl.[7] ................................................. A47B 96/06
[52] U.S. Cl. ............................... 248/229.15; 248/231.71; 248/229.1; 248/125.1; 5/503.1
[58] Field of Search ........................... 248/125.1, 125.8, 248/302, 229.16, 229.15, 227.4, 230.7, 231.71, 229.11, 231.31, 231.81; 5/503.1; 403/165, 377

[56] References Cited

U.S. PATENT DOCUMENTS

| | | | |
|---|---|---|---|
| 2,607,881 | 8/1952 | Anderson | 5/503.1 |
| 2,913,740 | 11/1959 | Eldridge | 5/503.1 |
| 3,030,639 | 4/1962 | Boyer | 248/231.71 |
| 3,565,380 | 2/1971 | Langren | 248/229.1 |
| 4,190,224 | 2/1980 | LeBlanc et al. | 248/227.3 |
| 4,593,422 | 6/1986 | Wolpert, Jr. | 5/503.1 |
| 4,840,391 | 6/1989 | Schneider | 280/304.1 |
| 4,945,592 | 8/1990 | Sims et al. | 5/503.1 X |
| 5,288,093 | 2/1994 | Gross | 248/125.1 X |
| 5,588,166 | 12/1996 | Burnett | 5/503.1 |

*Primary Examiner*—Leslie A. Braun
*Assistant Examiner*—Gwendolyn Baxter
*Attorney, Agent, or Firm*—Watson Cole Grindle Watson, P.L.L.C.

[57] ABSTRACT

The assembly is used with a conventional intravenous stand having a generally vertically disposed pole. An upper support includes a first body having a bore receiving an adjusting screw adapted to engage the pole for securing the upper support in adjusted position on the pole. A support member defines a downwardly facing recess adapted to fit over the upper edge of the headboard of a hospital bed. The support member also includes a pair of free ends slidably supported within bores in the body and held in place by clamping screws. A lower support includes a second body having a bore receiving a second adjusting screw adapted to engage the pole. A pair of independently movable support arms have outer ends which are movable toward and away from one another. The inner ends of the arms are slidably supported within bores in the second body and are held in place by clamping screws.

2 Claims, 2 Drawing Sheets

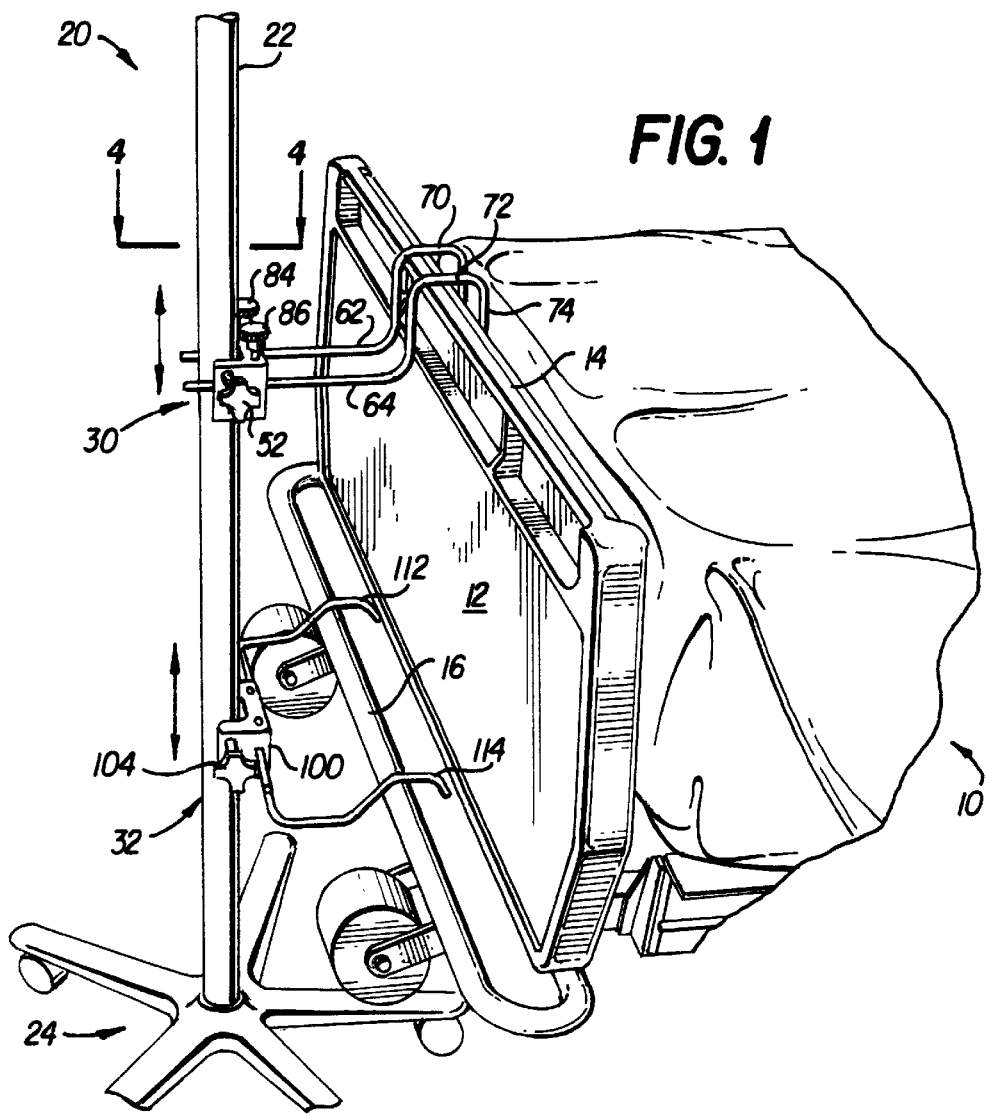
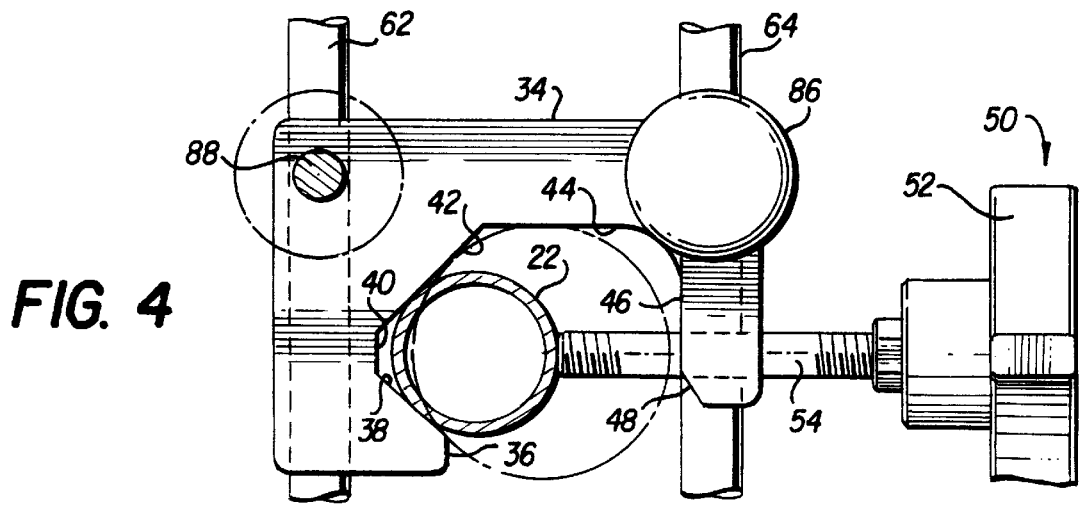

INTRAVENOUS STAND SUPPORT ASSEMBLY

This application claims priority of provisional application Ser. No. 60/062,713 filed Oct. 22. 1997.

BACKGROUND OF THE INVENTION

The present invention relates to an intravenous stand support assembly for use with a conventional intravenous (IV) stand having a generally vertically disposed pole supported at its lower end on a wheeled base and having at its upper and suitable means for supporting intravenous equipment therefrom.

When a patient in a hospital is on IV therapy, the common practice is to position a conventional IV stand near the headboard of a hospital bed which supports the patient. This is satisfactory as long as the bed does not need to be moved. However, it often becomes necessary to move the bed to transport the patient from one location to another within a hospital. When a bed is moved, it is necessary to roll the IV stand along the floor as the bed moves. Pushing the IV separately from the bed is not convenient and can cause the stand to fall over.

Accordingly, it is a principal objective of the invention to facilitate the transport of patients on IV therapy by providing an assembly which enables the IV stand to be supported by the bed above the floor using the bed's capability to be electromechanically raised and lowered, so that the stand moves along with the bed and there is not danger of the stand falling over.

It is a further objective to provide an assembly which maybe used with a variety of IV stands and beds of various dimensions without requiring any modifications in the structure of either the beds or the IV stands.

SUMMARY OF THE INVENTION

The assembly of the invention includes an upper support including support means in the form of an integral bent rod having an outer end defining a downwardly facing recess for receiving the upper edge of the headboard of a hospital bed. A clamping screw is provided for clamping the upper support at a desired adjusted vertical position along an IV stand pole. The upper support may be adjusted vertically along the pole, and the bent rod may be moved toward and away from the pole and clamped in position to accommodate different sizes and shapes of the headboard of the bed.

The assembly also includes a lower support including a pair of independently operable arms having outer ends which can be moved toward and away from one another and clamped in position relative to one another. A clamping screw is provided for clamping the lower support in desired adjusted vertical position along the IV pole. The lower support may also be adjusted angularly with respect to the pole, if so desired.

The upper and lower supports can be easily mounted upon and removed from the IV pole and can be readily adjusted relative to the pole. The clamping mechanisms of the present invention will not interfere with any apparatus which is normally supported by the IV stand.

In use, the bed or gurney is placed in its lowest position by using the existing mechanisms employed for raising and lowering the bed or gurney. The IV stand is then rolled toward the bed and the assembly is adjusted relative to the IV pole so that the upper and lower supports of the assembly are adapted to engage the bed. The lower support is adapted to engage a lower portion of the bed, and the upper support is adapted to engage the headboard of the bed. The engagement of the lower support with the bed serves to support the IV stand on the bed, and the upper support serves to provide stability to the assembly in a direction at a right angle to the IV pole.

When the bed is then raised with its existing mechanism, the IV pole will be lifted off of the floor and the assembly remains securely connected to the bed. The distance that the outer ends of the arms of the lower arm are apart can be adjusted in accordance with a particular bed and provides stability in a direction parallel with the headboard from side to side of the bed.

Once the IV stand has been elevated when the bed is raised, the wheels of the IV stand are above the floor. The bed and IV stand can then be moved as a single unit. When it is desired to return the IV stand to normal service, the bed is lowered to its normal position so that the wheels of the IV stand are again in contact with the floor. The assembly can then be released from the IV pole by releasing the clamping screws holding the upper and lower supports in place.

BRIEF DESCRIPTION OF THE DRAWINGS

FIG. 1 is a top perspective view showing a hospital bed and a conventional IV stand supported thereon by the invention assembly;

FIG. 4 is a sectional view taken along line 4—4 of FIG. 1 and being partly broken away.

DESCRIPTION OF THE PREFERRED EMBODIMENT

Figure 2:
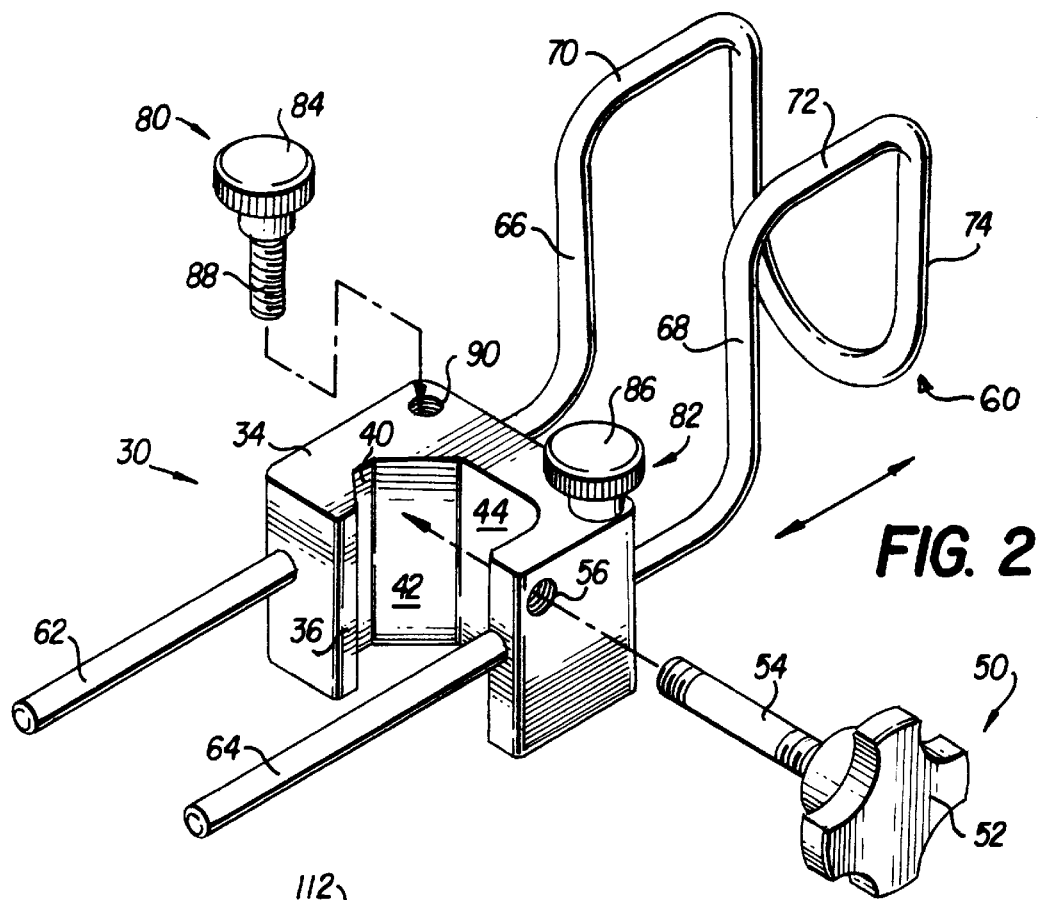
FIG. 2 is a top perspective exploded view showing the upper support.

Referring to the drawings wherein like reference characters designate similar parts through the several views, there is shown in FIG. 1 a conventional hospital bed indicated generally by reference numeral 10, the bed having a headboard 12 having an upper edge 14. A horizontal bar 10 is connected to the frame of the bed and projects outwardly of the headboard. A conventional IV stand is indicated generally by reference numeral 20 and includes a vertically extending pole 22 which is supported at its lower end on a wheeled base 24. The upper end of pole 22 (not shown) is provided with the usual means for supporting intervenous equipment. The hospital bed and the IV stand are of well-known construction.

The assembly of the invention comprises an upper support 30 and a lower support 32 each of which is independently adjustable so that they may be individually moved into any desired vertical position along the pole of the IV stand. The IV stand is shown in FIG. 1 as being supported on the bed by the upper and lower supports for transport of the IV stand along with the bed when the bed is moved to another location.

As seen in FIG. 2, the upper support comprises a rigid comprises a rigid body 34 formed of a block of metallio material such as aluminum. As seen most clearly by reference to FIGS. 2 and 4, body 34 is provided with a recess therein defined by adjoining flat surfaces 36, 38, 40, 42, 44, 46 and 48. This recess permits the pole to enter into the recess from a lateral direction and then be clamped into the position shown in FIG. 4. A clamping screw 50 includes a knob 52 with a threaded shank 54 which is received within a threaded hole 56 extending through the block and opening into the recess formed in body 34. It is apparent that the clamping screw serves as adjusting means and is adapted to clamp the upper support on the IV pole as seen in FIG. 4 in any desired adjusted vertical position.

As seen in FIG. 2, the upper support also includes a first support means in the form of an integral rigid bent rod 60 formed of a suitable metal such as steel. Rod 60 includes a pair of free ends 62 and 64 which are slidably supported within through bores formed in body 34. Rod 60 includes integral vertically extending portions 66 and 68 which join with horizontal portions 70 and 72 which in turn join with an integral generally U-shaped portion 74 which joins portions 70 and 72. It is noted that portions 66, 68, 70, 72 and 74 define a downwardly facing recess at the outer end of rod 80 which is adapted to receive the upper edge 14 of the headboard 12 of the hospital bed as illustrated in FIG. 1.

A pair of clamping screws 80 and 82 are provided with knobs 84 and 86 respectively. Each of the knobs is provided with a threaded shank such as 88 connected to knob 84. These threaded shanks are received within suitable threaded bores such as 90, these threaded bores interacting with the through bores which slidably receive the ends 62 and 64 of rod 60. For the sake of illustration, the knob of clamping screw 80 has been removed in FIG. 4 and the threaded shank 88 thereof is shown. This arrangement permits the outer end of rod 60 to be moved toward and away from the IV pole whereupon it can be clamped in position by screws 80 and 82 depending on the construction of the hospital bed. It is apparent that the bottom ends of clamping screws 80 and 82 are adapted to engage theportion of ends 62 and 64 of the rod 60 which are slidably disposed within the through bores in body 34.

Figure 3:
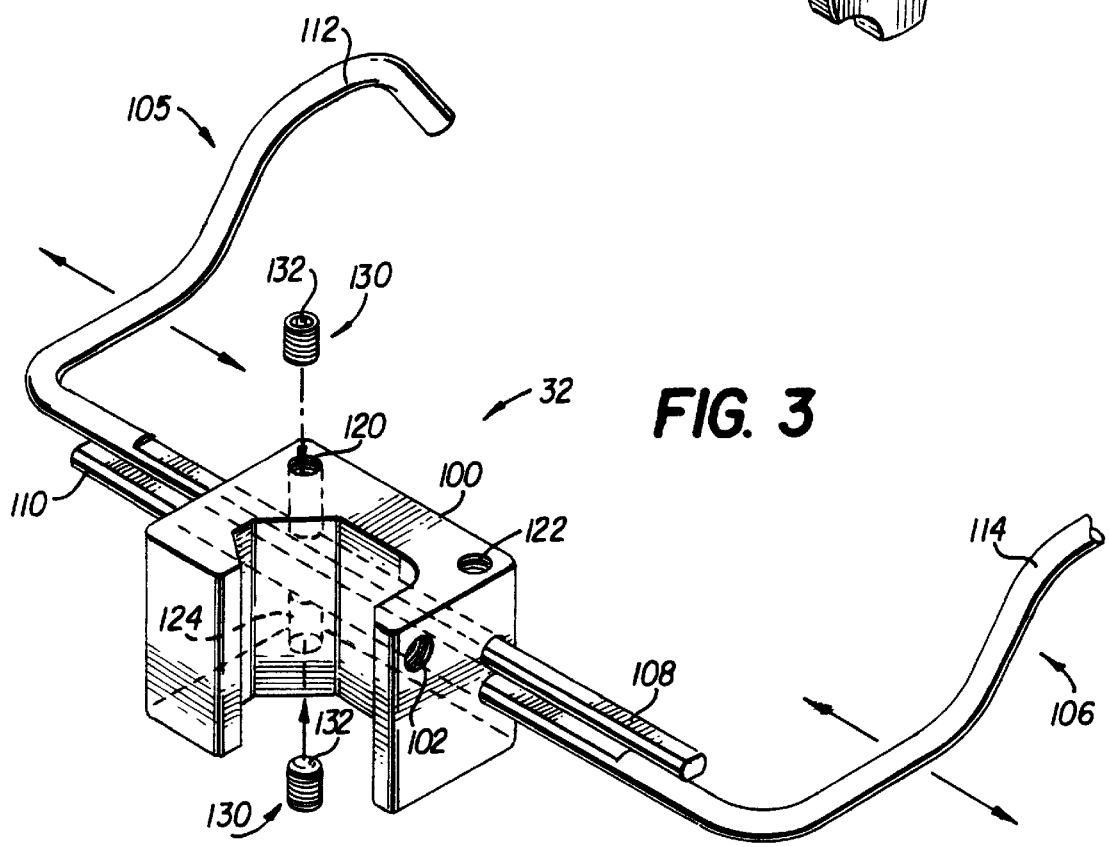
FIG. 3 is a top perspective exploded view showing the lower support.

Referring now to FIG. 3, the lower support includes a rigid body 100 similar to block 34 shown in FIG. 2 in that body 100 has a recess formed therein similar to that formed in body 34 for receiving an IV pole therein. Body 100 also has a threaded hole 102 formed therein similar to hole 56 in body 34 for receiving a clamping screw 104 as shown in FIG. 1 which operates in a manner identical to clamping screw 50 previously described for adjusting the position of the lower support along an IV pole.

The second support means comprises a pair of independently movable arms 105 and 106 having inner ends 108 and 110 respectively which are slidably disposed within suitable through bores formed in body 100. The outer ends of arms 104 and 106 include similar arched portions 112 and 114 respectively which are adapted to receive the bar 16 on the hospital bed. The specific configuration of the outer ends of arms 104 and 106 may be varied so as to cooperate with structure present at the headboard area of the hospital bed which is utilized to support an IV stand. The outer ends of the arms can be moved toward and away from one another as desired.

Body 100 is provided with a first pair of threaded bores 120 and 122 formed in the upper face of the body which intersect the through bore in body 100 which receives the inner end 108 of arm 104. A similar pair of threaded bores, one of which, 124, is visible in FIG. 3 are provided in the opposite face of the body and which intersect the through bore in body 100 which receives the inner end 110 of arm 108. Each of bores 120, 122 and 124 received a threaded stud 130 therein, the studs having a hexagonal socket 132 formed in one end thereof for receiving an alien wrench. The studs serve as manually operated clamping members for engaging the inner ends of the arms to hold the arms in any desired position. The inner ends of arms 108 and 110 may be provided with flats formed thereon for providing better contact between the inner ends of the studs and the inner ends of the arms.

The invention has been described with reference to a preferred embodiment. Obviously, various modifications, alterations and other embodiments will occur to others upon reading and understanding this specification. It is our intention to include all such modifications, alterations and alternate embodiments insofar as they come within the scope of the appended claims or the equivalent thereof.

What is claimed is:

1. An intravenous stand support assembly for use with an intravenous stand having a generally vertically disposed pole, said assembly comprising, an upper support and a lower support for engaging spaced portions of the pole, said upper support including a first rigid body having a first body recess formed therein for receiving the pole, first adjusting means for securing said upper support in a first adjusted position on the pole, a first support means in the form of an integral member having spaced parallel inner ends movably supported by said first body, said member also including at its outer end spaced portions defining a downwardly facing recess for receiving the upper edge of the headboard of a hospital bed, said outer end of the integral member being movable toward and away from said first body, first clamping means for clamping said integral member in fixed relation to said fist body, said lower support including a second rigid body having a second body recess formed therein for receiving the pole, second adjusting means for securing said lower support in a second adjusted position on the pole, a second support means movably supported b said second body, said second support means including a pair of independently movable arms movably supported by said second body, each of said arms including an outer end adapted to engage a portion of the hospital bed, said outer ends of said arms being movable toward and away from one another, and a second clamping means for clamping said arms in fixed relation to said second body.

2. The assembly as defined in claim 1 wherein each of said first and second bodies includes a top and bottom surface joined by a side surface, the body recess in each body opening at said top and bottom surfaces and also at said side surface so that the pole can enter into the body recess from a lateral direction.

* * * * *